(12) United States Patent
Jaques et al.

(10) Patent No.: US 7,838,492 B2
(45) Date of Patent: *Nov. 23, 2010

(54) RECOMBINANT CANINE THYROID STIMULATING HORMONE AND METHODS OF PRODUCTION AND USE THEREOF

(76) Inventors: John Scott T. Jaques, 1413 Clement Ct., College Station, TX (US) 77840; Donald L. Jarvis, 43 Snowy View Rd., Laramie, WY (US) 82070

(*) Notice: Subject to any disclaimer, the term of this patent is extended or adjusted under 35 U.S.C. 154(b) by 113 days.

This patent is subject to a terminal disclaimer.

(21) Appl. No.: 12/351,441

(22) Filed: Jan. 9, 2009

(65) Prior Publication Data

US 2010/0196276 A1 Aug. 5, 2010

Related U.S. Application Data

(63) Continuation of application No. 11/383,081, filed on May 12, 2006, now Pat. No. 7,479,549, which is a continuation-in-part of application No. 11/361,064, filed on Feb. 23, 2006, now abandoned.

(60) Provisional application No. 60/656,576, filed on Feb. 23, 2005.

(51) Int. Cl.
*A61K 38/16* (2006.01)
*G01N 33/00* (2006.01)
*C07K 1/00* (2006.01)

(52) U.S. Cl. ............... 514/8; 436/86; 436/87; 530/397

(58) Field of Classification Search ............... None
See application file for complete search history.

(56) References Cited

U.S. PATENT DOCUMENTS 7,479,549 B2 1/2009 Jaques et al. ............... 536/23.1

FOREIGN PATENT DOCUMENTS

WO 9806835 2/1998

WO 0052135 A2 9/2000

OTHER PUBLICATIONS

Ngo et al.; The Protein Folding Problem and Tertiary Structure Prediction, Merz et al. (ed.); Birkhauser; Boston, MA; pp. 433 and 492-495, 1994.
Yang et al., Domestic Animal Endocrinology 18; pp. 379-393, 2000.
Hollister, J. and Jarvis, D.L., "Enginerering Lepidopteran Insect Cells for Sialoglycoprotein Production by Genetic Transformation With Mammalian β1,4-Galactosyltransferase and α2,6-sialyltransgeras Genes", Glycobiology vol. 11 No. 1, pp. 1-9, 2001.
Breitbach, K. and Jarvis, D.L., "Improved Glycosylation of a Foreign Protein by Tn-5B1-4 Cells Engineered to Express Mammalian Glycosyltransferases", Biotechnol. Bioengr.74, pp. 230-239, 2001.
Seo, N.-S., Hollister, J.R., and Jarvis, D.L., "Mammalian Glycosyltransferase Expression Allows Sialoglycoprotein Production by Baculovirus-Infected Insect Cells", Prot. Expr. Pur. 22, pp. 234-241, 2001.
Jarvis, D.L., Howe, D. and Aumiller, J.J., "Novel Baculovirs Expression Vectors That Provide Sialylation of Recombinant Glycoproteins in Lepidopteran Insect Cells", J. Virol. 75, pp. 6223-6227, 2001.
"Hit the Ground Running"; Ultimate Human ORF Clones-Sequence-Verified and Ready To Use; Initroge Life Technology; Expressions, A Newsletter for Gene Cloning, Expression, and Analysis; vol. 10, Issue 1, 20 pages, Feb. 2003.

*Primary Examiner*—Suzanne M Noakes
*Assistant Examiner*—Jae W Lee
(74) *Attorney, Agent, or Firm*—Baker Botts L.L.P.

(57) ABSTRACT

The invention includes a nucleic acid having a sequence at least 98% homologous to SEQ ID NO: 1, which encodes the α subunit of canine thyroid stimulating hormone (TSH). The invention also includes a nucleic acid having a sequence at least 98% homologous to SEQ ID NO: 2, which encodes the β subunit of canine TSH. The invention also includes a method of producing a recombinant canine thyroid stimulating hormone (rcTSH) subunit by expressing a nucleic acid having a sequence of SEQ ID NO: 1 and a nucleic acid having a sequence of SEQ ID NO: 2 in a transgenic insect cell modified to sialylate proteins and producing a sialylated rcTSH subunit. The insect cell may be a lepidopteran cell. The rcTSH may be used for diagnosis and treatment. It may be used to diagnose canine hypothyroidism.

5 Claims, 2 Drawing Sheets

RECOMBINANT CANINE THYROID STIMULATING HORMONE AND METHODS OF PRODUCTION AND USE THEREOF

CROSS-REFERENCE TO RELATED APPLICATION

This application is a continuation of U.S. patent application Ser. No. 11/383,081 filed May 12, 2006; now U.S. Pat. No. 7,479,549 Granted Jan. 20, 2009; which claims priority under 35 U.S.C. §119 to U.S. Provisional Application No. 60/656,576, filed Feb. 23, 2005. U.S. patent application Ser. No. 11/383,081 is also a continuation-in-part of U.S. patent application Ser. No. 11/361,064, filed Feb. 23, 2006, now abandoned.

STATEMENT OF GOVERNMENT INTEREST

Portions of the present invention were supported by funding from the National Institutes of Health. The US government may have certain rights in the invention.

TECHNICAL FIELD

The present invention, in selected embodiments, relates to recombinant canine thyroid stimulating hormone (rcTSH), methods of producing the hormone, including production in transgenic lepidopteron insect cells, such as from cell lines or insects, and potential uses, including use to test for hypothyroidism in canines.

BACKGROUND OF THE INVENTION

Hypothyroidism is one of the most common canine endocrine disorders. To determine hypothyroidism, many practicing veterinarians use several different tests to arrive at a diagnosis. These tests include thyroxine (T4), triiodothyronine (T3), thyroglobulin autoantibody (TgAA), canine thyrotropin (cTSH), free thyroxine (Free T4), Free thyroxine by dialysis (Free T4D), reverse triiodothyronine (rT3), and reverse thyroxine (rT4). Most labs do not provide all of these tests. Therefore, the veterinarian must use whatever test results the lab provides to determine the thyroid status of the animal. In the past, TSH has been obtained from bovine pituitaries and used to stimulate the thyroid gland to produce T4. Based on this T4 stimulation test, the veterinarian can determine whether an animal has primary hypothyroidism.

Although the T4 stimulation tests remains, in principle, a viable way to diagnose hypothyroidism, bovine TSH is no longer considered an acceptable test component. Because of the pituitary's location, bovine pituitary derivatives pose a particular danger for transmission of bovine spongioform encephalitis ("BSE", commonly known as "mad cow disease"). Bovine products may also transmit rabies and other diseases. They also suffer from cost ($70-$80 per dose) and availability problems. Even when bovine TSH is available, the purity and potency varies greatly from lot to lot, making reliable testing difficult. Further, bovine TSH has not been approved for use in the canine. While human recombinant TSH may be used in the place of canine TSH in this and other applications, it is expensive (at least $130 per dose). Both bovine and human TSH may invoke an immune response after the first administration, interfering with repeated testing or treatment.

To overcome the problems associated with bovine TSH, various systems have been developed to produce recombinant TSH, including an *E. coli* system and a conventional baculovirus-insect cell system. However, neither system can produce sialylated recombinant TSH, which is necessary for an efficacious in vivo test in any mammal. The un-sialylated TSH may not be used as a direct substitute for bovine TSH in previous methods designed for bovine TSH methods. In fact, the un-sialylated insect-specific glycans on TSH produced with the previous baculovirus-insect system would signal its rapid clearance from the canine circulatory system. Although sialylated TSH is currently produced in mammalian cells, these cells tend to produce protein only at low levels and are expensive to cultivate.

SUMMARY

In one embodiment, the invention includes a nucleic acid having a sequence at least 98% homologous to SEQ ID NO: 1. In another embodiment, the invention includes a nucleic acid having a sequence at least 98% homologous to SEQ ID NO: 2.

Another embodiment of the invention includes a method of producing an rcTSH subunit by expressing a nucleic acid having a sequence of SEQ ID NO: 1 and a nucleic acid having a sequence of SEQ ID NO: 2 in a transgenic insect cell modified to sialylate proteins and producing a sialylated rcTSH subunit.

For a better understanding of the invention and its advantages, reference may be made to the following description of exemplary embodiments.

BRIEF DESCRIPTION OF THE DRAWINGS

The current invention may be further understood through reference to the following description and drawings.

DESCRIPTION

Figure 1:
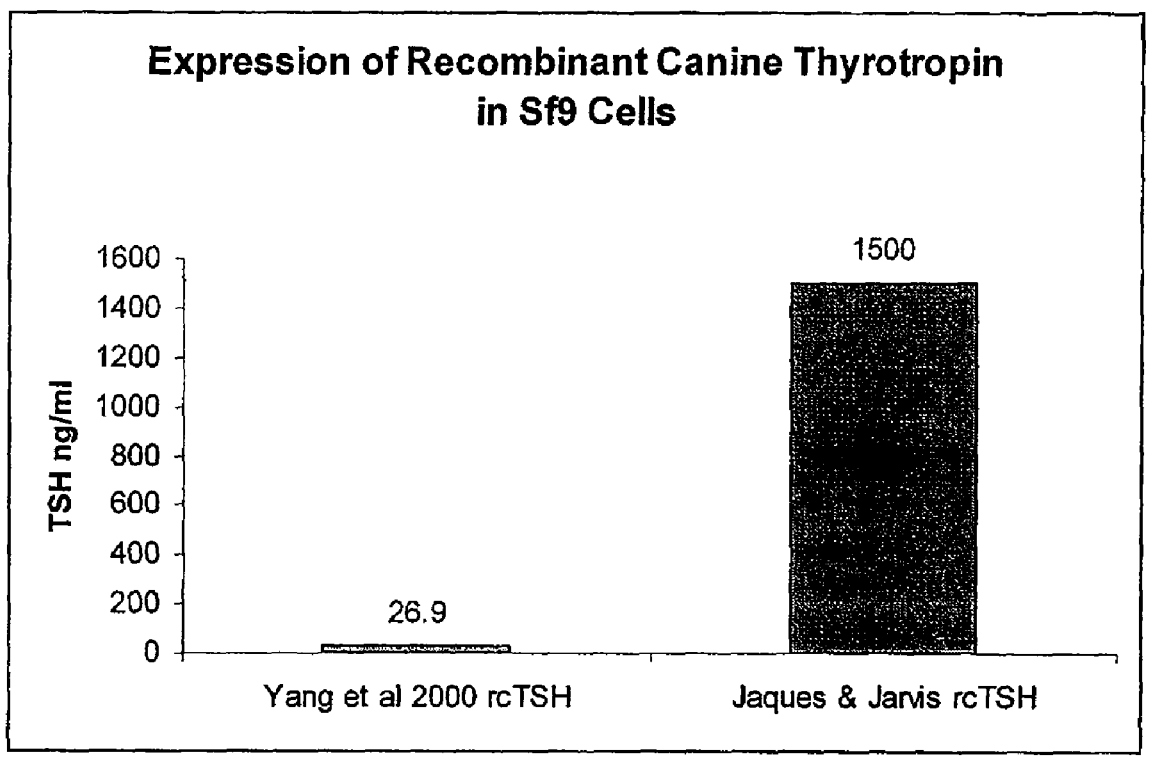
FIG. 1 is a graph comparing baculovirus-mediated TSH expression in Sf9 cells using the native canine TSH cDNA expressed with two baculoviruses under the control of the polyhedrin promoter or DNA having the sequence of SEQ ID NOS: 1 and 2, expressed with one baculovirus, with each gene placed under the control of a baculovirus immediate early (ie1) promoter.

The present invention, in one embodiment, relates to rcTSH that may be produced in lepidopteran cells, including cells from cells lines or in insects. Both the α and β subunits of rcTSH may be produced. Embodiments of the invention further include nucleic acids encoding each subunit which are optimized for expression in lepidoptera cells. (SEQ ID NO: 1 for α and SEQ ID NO: 2 for β). This is designed to provide higher expression levels in lepidoptera cells than when non-optimized rcTSH-encoding nucleic acids are used.

The optimized nucleic acid sequence for the α subunit is as follows:

GCAGATCTACCATGGACTGCTATCG-
CAAGTACGCGGCCGTGATATTGGCTGC-
CTTGAGCGTG TTCTTACACATATTGCACAGCTTTC-
CCGACGGCGAGTTTACGATGCAAGGCTGTCCGAA
TG CAAGTTGAAAGAGAACAAGTACTTTAG-
CAAATTGGGTGCGCCGATATACCAGTGCATGGGCT
GTTGCTTCTCGAGAGGCCTACCCGACGC-
CCGCGCGCAGCAAGAAAACGATGTTGGT-
GCCGAAG AACATTACGAGCGAAGCGACGTGT-
TGCGTGGCCAAAGCGTTTACGAAAGCTACGGTGAT

GGG CAACGCGAAAGTGGAAAACCACACGGAATGCCACTGTAGCACGTGCTACTATCACAAGAGCT AAGCGGCCGCACTAGTAGATCTGC (SEQ ID NO: 1).

The optimized nucleic acid sequence for the β subunit is as follows:

GCCCGCGGAGATCTACCATGACGGCGATCTACTTGATGAGCATGTTGTTTGGTTTAGCGTGC GGCCAGGCGATGAGCTTCTGCTTTCCGACGGAATACACCATGCACGTGGAGCGCAAAGAATG TGCCTACTGCTTGACGATTAACACAACGATTTGTGCCGGCTACTGCATGACGCGCGACATCA ATGGCAAGTTGTTCTTACCGAAATACGCGTTGAGCCAAGACGTGTGCACGTACCGCGACTTT ATGTACAAAACCGTGGAGATTCCCGGCTGCCCGAGACACGTGACCCCGTA CTTTAGCTACCC GGTGGCGGTGAGCTGTAAATGCGGCAAATGTAACACGGACTACAGCGACTGCATTCACGAAG CGATTAAGACGAACTATTGCACGAAACCGCAGAAATCGTACGTGGTTGGCTTTAGCAT CTAA GCGGCCGCACTAGTCCGCGGGC (SEQ ID NO: 2).

Although nucleic acids having SEQ ID NOS: 1 and 2 are optimized for expression in lepidopteran cells, some variation of the sequences may be possible without significant compromise of optimized expression levels. For example, alternative embodiments may include nucleic acids having sequences at least 98% homologous to SEQ ID NOS: 1 or 2, or at least 99% homologous to SEQ ID NOS: 1 or 2. Additional variant nucleic acids having sequences based on SEQ ID NOS: 1 or 2 may be produced which are optimized for other insect cell lines, particularly insect cell lines derived from insects closely related to lepidoptera. These nucleic acids may have sequences, for example, at least 90% homologous to SEQ ID NOS: 1 or 2 or at least 95% homologous to SEQ ID NOS: 1 or 2.

In developing alternative optimized nucleic acids for lepidopteran cells or other insect cells, some variation may be introduced in the protein coded. In general, more variation may be introduced in the β subunit than in the α subunit without loss of function, although embodiments in which there is more variation from the protein coded by SEQ ID NO: 1 than SEQ ID NO: 2 may also be acceptable. Accordingly, embodiments of the invention may be directed to nucleic acids optimized for expression in lepidopteran cells that encode a protein at least 90%, at least 95%, or at least 98% homologous to that encoded by SEQ ID NO: 1. Other embodiments may be directed to nucleic acids optimized for expression in lepidopteran cells that encode a protein at least 70%, at least 80%, at least 90%, or at least 95% homologous to that encoded by SEQ ID NO: 2.

Optimized nucleic acids encoding both the α and β subunits of rcTSH may be used to produce rcTSH. Additionally, the optimized sequences encoding the α subunit may be used to produce other proteins in which it is found (e.g. luteinizing hormone, follicle stimulating hormone, and chorionic gonadotrophin).

Other embodiments of the invention include optimized a or β subunit nucleic acids coupled to a promoter, particularly a promoter functional in a lepidopteran cell or another insect cell, including cells from cell lines or insects, or the insects (caterpillars) themselves, for which the sequence is optimized. Further embodiments may include additional regulatory elements functional in a lepidopteran or other insect cell. The relevant lepidopteran or insect cell may be modified to allow function of the selected promoter or regulatory element.

The α and β subunits may be delivered to the insect cell using a baculovirus. In particular, they may be delivered using a baculovirus that contains both the α and β subunits in the same virus. The subunits may both be expressed under control of an immediate early promoter. One embodiment of this baculovirus system involves positioning each subunit gene under the control of individual immediate early promoters oriented back to back in an immediate early baculovirus transfer plasmid. This plasmid is then used to produce the recombinant baculovirus by homologous recombination, using an established procedure. As shown in FIG. 1, this embodiment of the baculovirus system results in high expression levels.

Embodiments of the invention also include expression systems, such as plasmids, containing a nucleic acid encoding the α or β subunit of rcTSH optimized for expression in lepidopteran or other insect cells.

Methods of the present invention include production of the α and β subunit of rcTSH in an insect cell, in particular a lepidopteran cell, using a nucleic acid having a sequence optimized for expression in the cell, such as SEQ ID NOS:1 or 2. Accordingly, embodiments of the current invention may also include cells used in this method. These may include cells from cell lines derived from *Spodoptera frugiperda*, *Trichoplusia ni*, or other lepidopteran insects or cells from the insects themselves. In particular, it may include insect cells, such as lepidopteran cells, containing an nucleic acid having one or more sequences encoding the α or β subunit of rcTSH and optimized for expression in the insect cell. For example, it may include such a cell containing SEQ ID NO: 1 and/or SEQ ID NO: 2.

One example method of rcTSH production involves expression of an optimized nucleic acids in lepidopteran cells previously modified to enable sialoglycoprotein production. rcTSH or its subunits may then be isolated from the cells. This rcTSH may have many uses. For example, it may not be cleared as quickly from the body when administered to a canine. This may serve as the basis for in vivo uses. In one embodiment it may be used in a standard hypothyroidism test in a manner analogous to use of bovine TSH.

It will be understood that any other cell type which naturally sialylates proteins or has been enabled to do so might also be used to produce sialylated rcTSH. For example, transgenic dipteran cells may be used, such as S2 cell line derivatives. Additionally, the lepidopteran Sf9 cell line or a derivative cell line, such as the Sf SWT1, Sf SWT-3, Sf SWT-4, and Sf SWT-5 cell lines may be used. Also, analogous transgenic lines that could easily be produced using established cell lines from other lepidopteran insects, such as *Trichoplusia ni* may also be used. Cell lines and cells from insects may also be derived from analogous transgenic lepidopteran insects such as *S. frugiperda*, *T. ni*, and *B. mori*. Finally, the unmodified or transgenic lepidopteran insects (caterpillars), themselves, such as *S. frugiperda*, *T. ni*, and *B. mori* could be orally infected with the baculovirus vectors described herein.

In one embodiment, the two nucleic acids are expressed in the same cell to produce rcTSH in that cell, for example using a baculovirus with the nucleic acids under control of an immediate early promoter. In other embodiments, the rcTSH a and/or β subunits may be expressed using one or more recombinant baculoviruses using any promoter active in insect cell lines or cells from insects.

The nucleic acids may be introduced into the lepidopteran cells in any manner which allows for their later expression. In one embodiment, the nucleic acid is a DNA molecule and is introduced by infection with a baculovirus. In another embodiment is a DNA molecule introduced by transfection.

rcTSH produced using the nucleic acids and methods described above may be used in both the treatment and diagnosis of canine disorders, or disorders in other animals, particularly closely related animals or those able to sustain a physiological response to canine TSH. For example, although the rcTSH of the invention was designed for use in diagnostic testing for hypothyroidism in canines, it may also prove useful for diagnostic testing in other animals which are responsive to canine TSH. rcTSH may be produced in sialylated form as described above, which may reduce clearance from the body of an animal. Sialylated rcTSH might also be used in various TSH-based treatments and other diagnostic assays using TSH, whether in vitro or in vivo.

rcTSH produced using the nucleic acids and methods described above may also be further modified, in particular to assist with treatment or diagnosis. Such modification may be performed on the rcTSH directly, such as chemical modification, or it may include the formulation of the rcTSH. For example, the rcTSH may be placed in a pharmaceutically acceptable carrier such as phosphate buffered saline (PBS).

In one particular embodiment, sialylated rcTSH may be used in diagnostic testing in a manner analogous to bovine TSH. Briefly, such testing may include measurement of T4 levels followed by administration of TSH. T4 levels may again measured after administration and compared to earlier levels to see if the administered TSH induced an increase in T4 levels. If an increase occurred, it is indicative of hypothyroidism.

EXAMPLES

The following examples are included to demonstrate specific embodiments of the invention. Those of skill in the art should, in light of the present disclosure, appreciate that many changes may be made in the specific embodiments which are disclosed and still obtain a like or similar result without departing from the spirit and scope of the invention.

Example 1

Optimized rcTSH Exhibits Increased Expression in Lepidopteran Cells

Nucleic acids having SEQ ID NOS: 1 and 2 were provided to Sf9 insect cells using the Nucleic acids having SEQ ID NOS: 1 and 2 were provided to Sf9 insect cells using a baculovirus containing both the α and β subunits. Expression of TSH was measured using the methods of Yang et al., cDNA cloning of canine common α gene and its co-expression with canine thyrotropin β gene in baculovirus expression system, *Domestic Animal Endocrinology* 18:379-393 (2000), which is incorporated by reference herein. A comparison of TSH expression using the methods of the present invention as compared to the methods of Yang et al. is provided in FIG. 1. Yang et al. achieved an expression of only 26.9 ng/ml of TSH. In contrast, when nucleic acids having SEQ ID NOS: 1 and 2 were used in a single baculovirus under control of an immediate early promoter, expression was 1500 ng/ml. In later tests, expression as high as 2000 to 6000 ng/ml was obtained.

Figure 2:
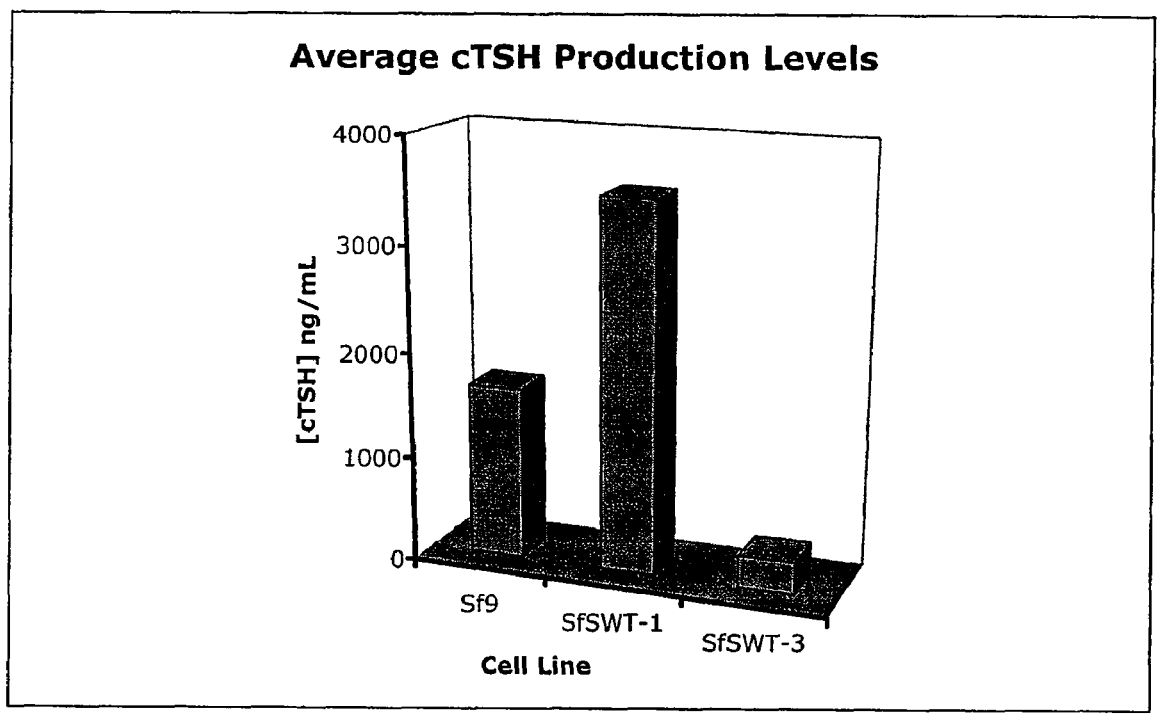
FIG. 2 is a graph showing average canine TSH production in three different insect cell lines.

Similar expression levels were observed in transgenic Sf9 cells capable of modifying the TSH, for example by sialylation. In one specific example, similar expression was observed in Sf SWT1 cells (also sold a Mimic™ Insect Cell Line, Invitrogen, Carlsbad, Calif.). See FIG. 2.

Fifty mL shake flask cultures of Sf9, SfSWT-1, or SfSWT-3 were infected with the recombinant baculovirus, AcP(+)DIEcTSHA/B at a multiplicity of infection of about 2-5 plaque forming units per cell. The virus was allowed to adsorb for about 6 h, and then the cells were harvested, fed with fresh medium, and incubated for 5 days. At that time, the cells were removed by low speed centrifugation and the cell free media were used to measure cTSH levels by a standard immunoassay. The cell growth medium used for this experiment was ESF-921 (Expression Systems).

Although only preferred embodiments of the invention are specifically described above, it will be appreciated that modifications and variations of the invention are possible without departing from the spirit and intended scope of the invention. One example would be a modification with dipteran cell lines.

The invention claimed is:

1. A method of diagnosing hypothyroidism in a canine comprising the step of:
   i) measuring T4 level in the canine;
   ii) administering sialylated recombinant Thyroid Stimulating Hormone (rcTSH) to the canine;
   iii) measuring T4 level in the canine after rcTSH administration; and
   iv) comparing the T4 level measurements in the canine before and after rcTSH administration, wherein a lack of increase or a decrease in T4 level after rcTSH administration is indicative of hypothyroidism, and wherein the sialylated rcTSH comprises a rcTSH protein β-subunit produced by the expression of a nucleic acid comprising the sequence of SEQ ID NO: 2.

2. A method of claim 1, wherein the sialylated rcTSH further comprises an rcTSH protein α-subunit produced by the expression of a nucleic acid comprising the sequence of SEQ ID NO: 1.

3. A method of claim 1, wherein the sialyated rcTSH is produced by an isolated lepidopteran cell comprising a nucleic acid comprising the sequence of SEQ ID NO: 2.

4. A method of claim 3, wherein the isolated lepidopteran cell further comprises a nucleic acid comprising the sequence of SEQ ID NO: 1.

5. A method of claim 1, wherein the sialylated rcTSH is produced by an isolated lepidopteran cell comprising a nucleic acid comprising the sequence of SEQ ID NO: 1.

* * * * *

SEQUENCE LISTING

```
<160> NUMBER OF SEQ ID NOS: 2

<210> SEQ ID NO 1
<211> LENGTH: 397
<212> TYPE: DNA
<213> ORGANISM: Canine Thyroid Stimulating Hormone

<400> SEQUENCE: 1
dgcagatcta ccatggactg ctatcgcaag tacgcggccg tgatattggc tgccttgagc      60
gtgttcttac acatattgca cagctttccc gacggcgagt ttacgatgca aggctgtccg     120
gaatgcaagt tgaaagagaa caagtacttt agcaaattgg gtgcgccgat ataccagtgc     180
atgggctgtt gcttctcgag agcctacccg acgcccgcgc gcagcaagaa aacgatgttg     240
gtgccgaaga acattacgag cgaagcgacg tgttgcgtgg ccaaagcgtt tacgaaagct     300
acggtgatgg gcaacgcgaa agtggaaaac cacacggaat gccactgtag cacgtgctac     360
tatcacaaga gctaagcggc cgcactagta gatctgc                              397
```

```
<210> SEQ ID NO 2
<211> LENGTH: 457
<212> TYPE: DNA
<213> ORGANISM: Canine Thyroid Stimulating Hormone

<400> SEQUENCE: 2
dgcccgcgga gatctaccat gacggcgatc tacttgatga gcatgttgtt tggtttagcg        60
tgcggccagg cgatgagctt ctgctttccg acggaataca ccatgcacgt ggagcgcaaa       120
gaatgtgcct actgcttgac gattaacaca acgatttgtg ccggctactg catgacgcgc       180
gacatcaatg gcaagttgtt cttaccgaaa tacgcgttga gccaagacgt gtgcacgtac       240
cgcgacttta tgtacaaaac cgtggagatt cccggctgcc cgagacacgt gaccccgtac       300
tttagctacc cggtggcggt gagctgtaaa tgcggcaaat gtaacacgga ctacagcgac       360
tgcattcacg aagcgattaa gacgaactat tgcacgaaac cgcagaaatc gtacgtggtt       420
ggctttagca tctaagcggc cgcactagtc cgcgggc                                457
```